United States Patent

Ichikawa et al.

[11] Patent Number: 5,691,763
[45] Date of Patent: Nov. 25, 1997

[54] TERMINATED CABLE PORTION INSPECTION DEVICE FOR STRIPPED TERMINAL CRIMPING MACHINE

[75] Inventors: Yoshihide Ichikawa; Hideki Ohmori, both of Yokkaichi; Tuneyoshi Takahashi; Kiyohide Abe, both of Tokyo, all of Japan

[73] Assignees: Sumitomo Wiring Systems, Ltd.; Kabushiki Kaisha Meidensha, both of Japan

[21] Appl. No.: 524,517

[22] Filed: Sep. 7, 1995

[30] Foreign Application Priority Data

Sep. 14, 1994 [JP] Japan ................. 6-220600
Sep. 14, 1994 [JP] Japan ................. 6-220601

[51] Int. Cl.[6] ................................. H04N 7/18
[52] U.S. Cl. .................... 348/86; 348/125; 382/141
[58] Field of Search .................. 348/86, 92, 94, 348/95, 125, 128, 131, 135, 143, 151, 161, 207, 335, 359, 370; 382/141, 152; H04N 7/18, 9/47

[56] References Cited

U.S. PATENT DOCUMENTS

| | | | |
|---|---|---|---|
| 4,232,336 | 11/1980 | Henry | 348/88 |
| 4,240,110 | 12/1980 | Henry | 348/88 |
| 4,415,926 | 11/1983 | Henry | 348/88 |
| 4,555,799 | 11/1985 | Kodama et al. | 382/141 |
| 4,636,847 | 1/1987 | Magi et al. | 382/165 |
| 4,731,856 | 3/1988 | Lloyd et al. | 382/141 |
| 4,988,202 | 1/1991 | Nayar et al. | 348/86 |
| 5,293,220 | 3/1994 | Fukuda et al. | 382/141 |
| 5,377,278 | 12/1994 | Ichikawa | 348/92 |
| 5,608,817 | 3/1997 | Yamaoka et al. | 382/141 |

FOREIGN PATENT DOCUMENTS

| | | |
|---|---|---|
| 0562614 | 9/1993 | European Pat. Off. . |
| 61-133844 | 6/1986 | Japan . |
| 61-133845 | 6/1986 | Japan . |
| 2189880 | 7/1990 | Japan . |

*Primary Examiner*—Tommy P. Chin
*Assistant Examiner*—Y. Lee
*Attorney, Agent, or Firm*—Jordan B. Bierman; Bierman, Muserlian and Lucas LLP

[57] ABSTRACT

A terminated cable portion inspection device (8) for a stripped terminal crimping machine, which is located on a bidirectional path (P) between a stripping portion and a terminal crimping portion and includes: an image pickup camera (11) having a high shutter speed; an illuminating device (12) including a pair of illuminating portions (20) on opposite sides of a photographing path (19) of the image pickup camera (11) for directing illumination in substantially the same direction as a photographing direction toward a cable end passing therethrough along the bidirectional path (P) and elongated in substantially the same direction as a longitudinal direction of the cable, and optical fibers (22) for guiding light to light projecting portions (23) of the illuminating portions (20); and a detector (13) including first and second sensors (31, 32) for detecting the cable end. Each of the illuminating portions (20) includes a transmitted light scattering plate (27) between each of the light projecting portions (23) and the bidirectional path (P), and a spacing (28) between each of the light projecting portions (23) and the transmitted light scattering portion (27) for diffusing light.

8 Claims, 17 Drawing Sheets

FIG. 19A
FIG. 19B
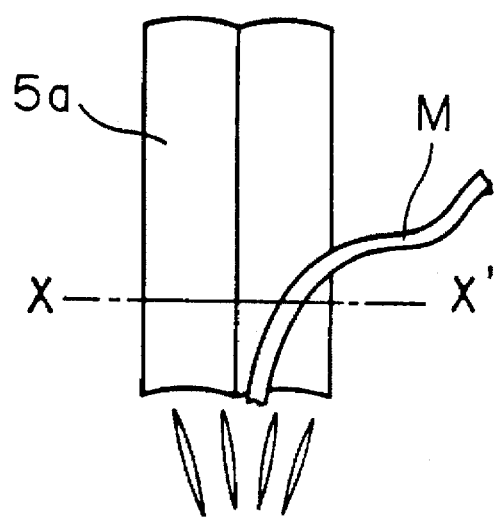
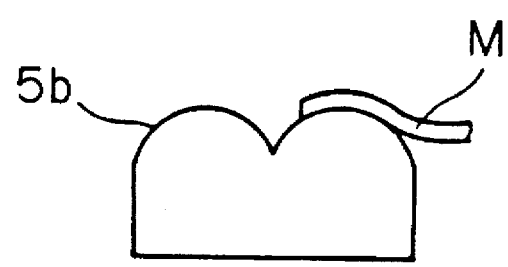
FIG. 20
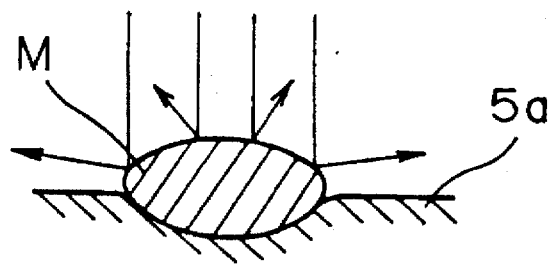

TERMINATED CABLE PORTION INSPECTION DEVICE FOR STRIPPED TERMINAL CRIMPING MACHINE

BACKGROUND OF THE INVENTION

1. Field of the Invention

The present invention relates to a terminated cable portion inspection device for a stripped terminal crimping machine which inspects stripped portions and terminal crimped portions of cables on a bidirectional path along which cable ends are transported.

2. Description of the Prior Art

Prior art inspection of the stripping conditions of a stripped portion at a cable end in which the coating is removed and the crimping conditions of a terminal crimped portion in which a crimp terminal is crimped to the stripped portion generally involves photographing the stripped portion and terminal crimped portion by an image pickup means such as a television camera and two-dimensional CCD camera, displaying the image photographed by the image pickup means on a monitoring television receiver, processing the image by an image processing means, judging whether or not the stripping and crimping conditions are defective, and displaying the result of judgement by means of a printer or display unit.

A device for such inspection includes a keyboard for operation which is used to input program data and the like required for image processing.

This type of inspection device is disclosed in for example Japanese Patent Application Laid-Open No. 61-133844 (1986). In this disclosure, a stripping portion strips the coating of a cable at a cable end held by a cable holding portion of an arm. The arm is pivoted to transport the stripped portion of the cable at the cable end to a terminal crimping portion which in turn crimps a crimp terminal to the stripped portion. The arm is then pivoted in the opposite direction to transport the terminal crimped portion of the cable to the stripping position. The cable is transported by a predetermined length in a predetermined direction and cut in position. Cables are sequentially subjected to the stripping and terminal crimping by the similar procedure.

The inspection device for inspecting the stripping and crimping condition is provided on a bidirectional path along which the cable is transported between the stripping portion and terminal crimping portion.

The inspection device comprises a light source and a television camera on opposite sides of the bidirectional path, and a photosensor including a light projector and a light receiver on opposite sides thereof for detecting a cable photographing timing. The photosensor detects the stripped portion and terminal crimped portion passing therethrough, and the light source emits light in response to the detection output of the photosensor. The television camera photographs the silhouette image of the stripped and terminal crimped portions, and an image processor captures and processes the silhouette image. In this manner, whether or not the stripping and crimping conditions are defective is judged.

However, the inspection device disclosed in Japanese Patent Application Laid-Open No. 61-133844 is of the type wherein the silhouette image is captured, that is, only the outline information of the silhouette is captured. The inspection device receives a small amount of image information and is incapable of detecting crimping failures and cores extending off in the silhouette portion, resulting in inaccurate inspection.

Another inspection device is of the type wherein an object to be inspected is illuminated from the photographing direction of the image pickup means to capture a reflected image for receiving more image information. However, this inspection device is designed to photograph the stationary object to be inspected in a purpose-built space, which requires a wide spacing for installation of a lighting fixture. It is hence difficult to incorporate this inspection device on the bidirectional path between the stripping potion and the terminal crimping portion.

Further, the inspection device disclosed in Japanese Patent Application Laid-Open No. 61-133844 is of the type such that the single photosensor detects the stripped portion passing through a photographing position of the television camera in one direction (a first direction) along the bidirectional path and the terminal crimped portion passing through a photographing position of the television camera in the opposite direction (a second direction) along the bidirectional path. The detection positions are on the side of the cable holding portion of the arm which holds the cable end.

The cable end hold by the arm in cantilevered fashion is typically transported along the bidirectional path at high speeds of about 2000 mm/s. This causes the distal end of the cable moved in the first direction to deflect slightly rearwardly in the transport direction. On the other hand, the cable end moved in the second direction is weighted with the crimp terminal crimped thereto, causing the distal end of the cable to deflect by a greater amount rearwardly in the opposite transport direction.

Thus the photographing timings are different between the stripped portion and the terminal crimped portion. When the cable end transported at high speeds in both directions along the bidirectional path is detected in the same manner by the single photosensor on the side of the cable holding portion of the arm and photographed by the television camera, the images are not stably captured and, in the worst case, a portion to be photographed does not lie within the photographing range of the television camera.

SUMMARY OF THE INVENTION

According to a first aspect of the present invention, in a stripped terminal crimping machine including a stripping portion for stripping a coating at an end of a cable, a terminal crimping portion for crimping a crimp terminal to the stripped end of the cable, a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, and a terminated cable portion inspection device for photographing the cable end transported along the bidirectional path to inspect a stripped portion and a terminal crimped portion of the cable by image processing; the terminated cable portion inspection device comprises: an image pickup camera having a high shutter speed; a pair of illuminating portions on opposite sides of a photographing path of the image pickup camera for directing illumination in substantially the same direction as a photographing direction of the image pickup camera toward the cable end passing therethrough along the bidirectional path, the pair of illuminating portions being elongated in substantially the same direction as a longitudinal direction of the cable; an optical fiber for guiding light emitted from a light source to light projecting portions of the illuminating portions; a first sensor for detecting a timing of photographing the cable end transported in the first direction along the bidirectional path by the image pickup camera; and a second sensor for detecting a timing of photographing the cable end transported in the second direction along the bidirectional path by the image pickup camera, the first sensor and the second sensor being located in positions deviated from an optical axis of the image pickup camera.

According to a second aspect of the present invention, in a stripped terminal crimping machine including a stripping portion for stripping a coating at an end of a cable, a terminal crimping portion for crimping a crimp terminal to the stripped end of the cable, a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, and a terminated cable portion inspection device for photographing the cable end transported along the bidirectional path to inspect a stripped portion and a terminal crimped portion of the cable by image processing; the terminated cable portion inspection device comprises: an image pickup camera having a high shutter speed; a pair of illuminating portions on opposite sides of a photographing path of the image pickup camera for directing illumination in substantially the same direction as a photographing direction of the image pickup camera toward the cable end passing therethrough along the bidirectional path, the pair of illuminating portions being elongated in substantially the same direction as a longitudinal direction of the cable; a first sensor for detecting a timing of photographing the cable end transported in the first direction along the bidirectional path by the image pickup camera; and a second sensor for detecting a timing of photographing the cable end transported in the second direction along the bidirectional path by the image pickup camera, the first sensor and the second sensor being located in positions deviated from an optical axis of the image pickup camera, wherein the detection position of the first sensor is positioned in corresponding relation to a passing position of an end of the coating at the stripped cable end, and the detection position of the second sensor is positioned in corresponding relation to a passing position of an intermediate portion of a core crimping portion of the crimped crimp terminal.

Preferably, according to a third aspect of the present invention, the detection position of the first sensor is positioned in corresponding relation to a passing position of an end of the coating at the stripped cable end, and the detection position of the second sensor is positioned in corresponding relation to a passing position of an intermediate portion of a core crimping portion of the crimped crimp terminal.

Preferably, according to a fourth aspect of the present invention, each of the pair of illuminating portions includes: a transmitted light scattering plate between the bidirectional path and each of the light projecting portions projecting the light guided by the optical fiber; and a spacing between each of the light projecting portions and the transmitted light scattering plate for diffusing light.

Preferably, according to a fifth aspect of the present invention, each of the pair of illuminating portions includes: a transmitted light scattering plate between the bidirectional path and each of the light projecting portions projecting the light guided by the optical fiber; and a condenser lens between each of the light projecting portions and the transmitted light scattering plate for guiding the light projected from each of the light projecting portions in a direction at right angles to the transmitted light scattering plate.

Preferably, according to a sixth aspect of the present invention, the first sensor and the second sensor are positioned so that the cable end is detected by the first sensor and the second sensor when the cable end passes across the optical axis of the image pickup camera.

Preferably, according to a seventh aspect of the present invention, the terminated cable portion inspection device further comprises: an irregular reflector plate opposed to the illuminating portions, with the bidirectional path therebetween.

According to the present invention, the illuminating portions for directing illumination in substantially the same direction as the photographing direction of the image pickup camera toward the cable end passing therethrough along the bidirectional path are provided on both sides of the photographing path of the image pickup camera and are elongated in substantially the same direction as the longitudinal direction of the transported cable, thereby ensuring a sufficient brightness. The reflected image of the cable end being transported is satisfactorily captured by the image pickup camera having the high shutter speed. This achieves the provision of a great amount of image information, and the inspection using more correct image information.

Further, the optical fiber is designed to guide the light emitted from the light source to the light projecting portions of the illuminating portions. The illuminating portions which are compact in size may be readily incorporated in a small spacing in closer proximity to the bidirectional path of the cable end. This also insures a sufficient brightness and the size reduction of the terminated cable portion inspection device itself incorporated in the stripped terminal crimping machine.

The detecting position of the first sensor is positioned in corresponding relation to the passing position of the end of the coating at the stripped cable end, and the detecting position of the second sensor is positioned in corresponding relation to the passing position of the intermediate portion of the core crimping portion of the crimped crimp terminal. Such an arrangement provides the good photographing timing by the image pickup camera, whether the cable be transported in the first or second direction along the bidirectional path, and stabilized image capturing.

Additionally, each of the illuminating portions includes the transmitted light scattering plate between the bidirectional path and the light projecting portion projecting the light guided by the optical fiber, and the spacing between the light projecting portion and the transmitted light scattering plate for diffusing light. Otherwise, each of the illuminating portions includes the condenser lens between the light projecting portion and the transmitted light scattering plate for guiding the light projected from the light projecting portion in the direction at right angles to the transmitted light scattering plate. This provides illumination of more uniformly scattered light.

The irregular reflector plate opposed to the illuminating portions, with the bidirectional path therebetween, can irregularly reflect the light from the illuminating portions to function as sub-illumination. This also insures the sufficient brightness.

It is therefore an object of the present invention to provide a terminated cable portion inspection device for a stripped terminal crimping machine which is compact in size and of the type wherein a reflected image is captured.

It is another object of the invention to provide a terminated cable portion inspection device for a stripped terminal crimping machine which provides good photographing timing of an image pickup camera and stabilized image capturing.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 19A, 19B, 20 and 21 illustrate operation of the first preferred embodiment;

DESCRIPTION OF THE PREFERRED EMBODIMENTS

Figure 1:
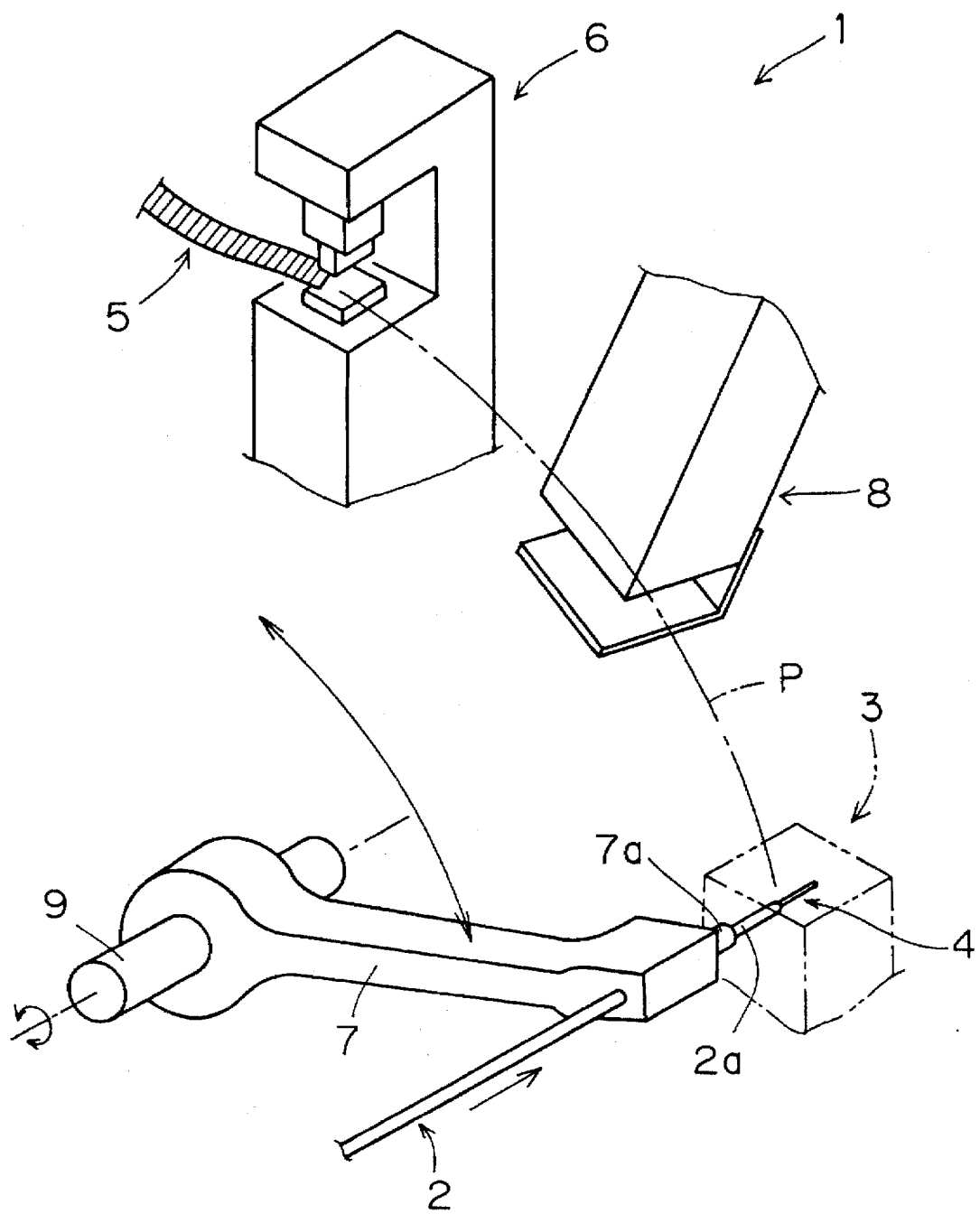
FIG. 1 schematically illustrates essential portions of a stripped terminal crimping machine according to a preferred embodiment of the present invention.

Preferred embodiments according to the present invention will now be described with reference to the drawings. Referring to FIGS. 1 to 7, a stripped terminal crimping machine 1, like the conventional machine, comprises a stripping portion 3 for stripping a coating 2a at an end of each cable 2 sequentially fed; a terminal crimping portion 6 for crimping a crimp terminal 5 to a stripped portion 4 at the stripped end of the cable 2; a transport arm 7 for holding the cable 2 adjacent one end thereof and serving as a transport mechanism for transporting the end of the cable 2 between the stripping portion 3 and the terminal crimping portion 6 in a reciprocal manner; and a terminated cable portion inspection device 8 located on a bidirectional path P of the end of the cable 2.

The stripping portion 3 suitably includes a cutting blade for severing the cable 2 and a stripping blade for cutting through the coating 2a, and is controlled to cut and strip the cable 2.

The terminal crimping portion 6 includes a crimping machine. The terminal crimping portion 6 feeds successive crimp terminals 5 one by one to a crimping position in the crimping machine and is controlled to crimp one crimp terminal 5 to the stripped portion 4.

The transport arm 7 includes a cable clamp portion 7a for releasably holding the cable 2. The transport arm 7 is pivoted on a support shaft 9, with the cable 2 held by the cable clamp portion 7a, and is controlled to transport the end of the cable 2 in a reciprocal manner along the bidirectional path P at high speeds (for example, about 2000 mm/s).

The terminated cable portion inspection device 8 includes an image pickup camera 11, such as a television camera and two-dimensional CCD camera, serving as an image pickup means for photographing the end of the cable 2 transported along the bidirectional path P; an illuminating means 12 for illuminating the end of the cable 2 transported along the bidirectional path P; and a detecting means 13 for detecting the photographing timing of the end of the cable 2 transported along the bidirectional path P.

The image pickup camera 11 employs a camera having a superfast shutter function such that the shutter speed is fast (for example, 1/30000 sec.), and is angularly adjustably mounted at a predetermined angle to a mounting bracket 14 on the base of the stripped terminal crimping machine 1. The image pickup camera 11 includes a camera body 15, an extension tube 16, and a lens portion 17.

Figure 4:
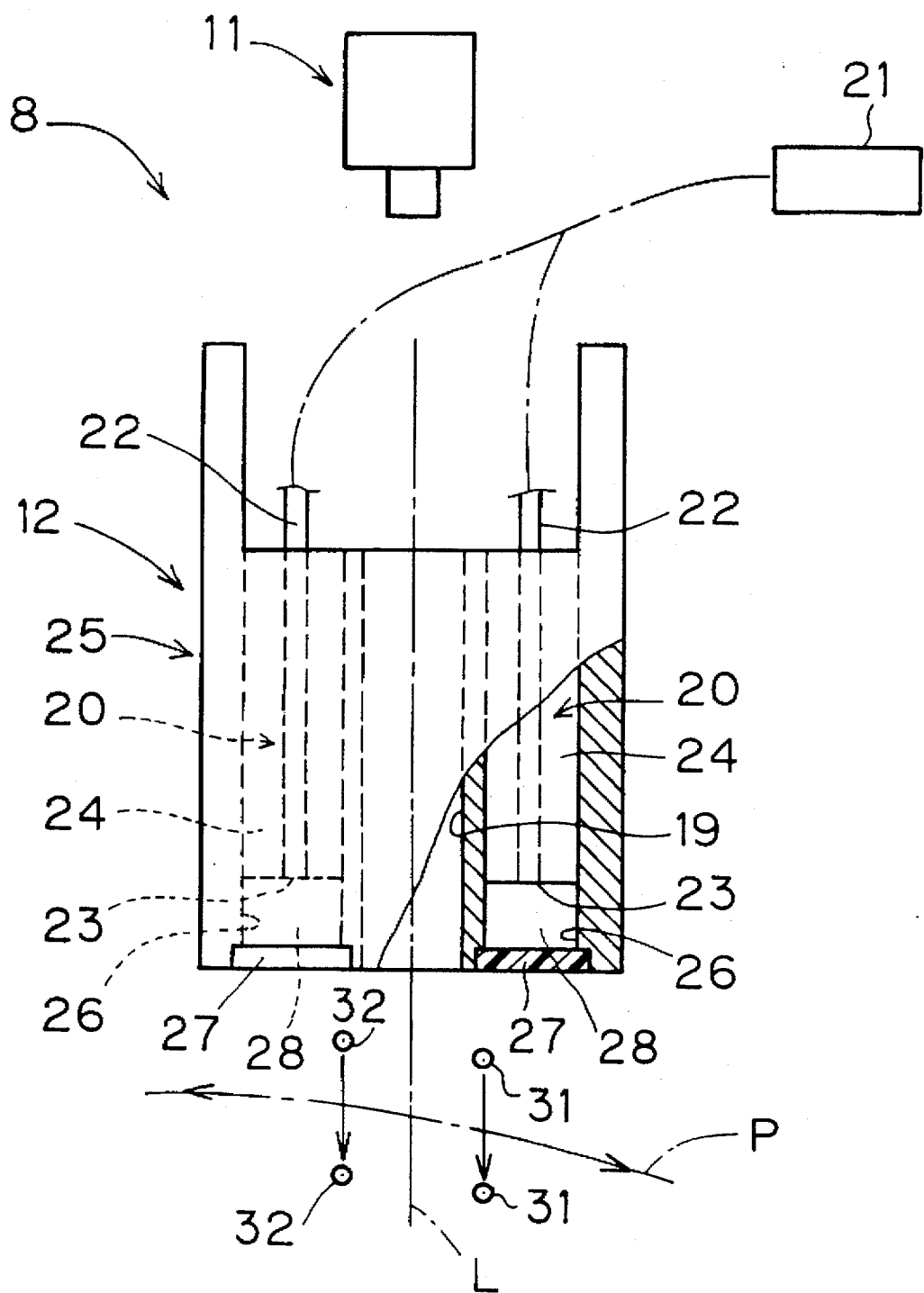
FIG. 4 illustrates an illuminating means.
Figure 5:
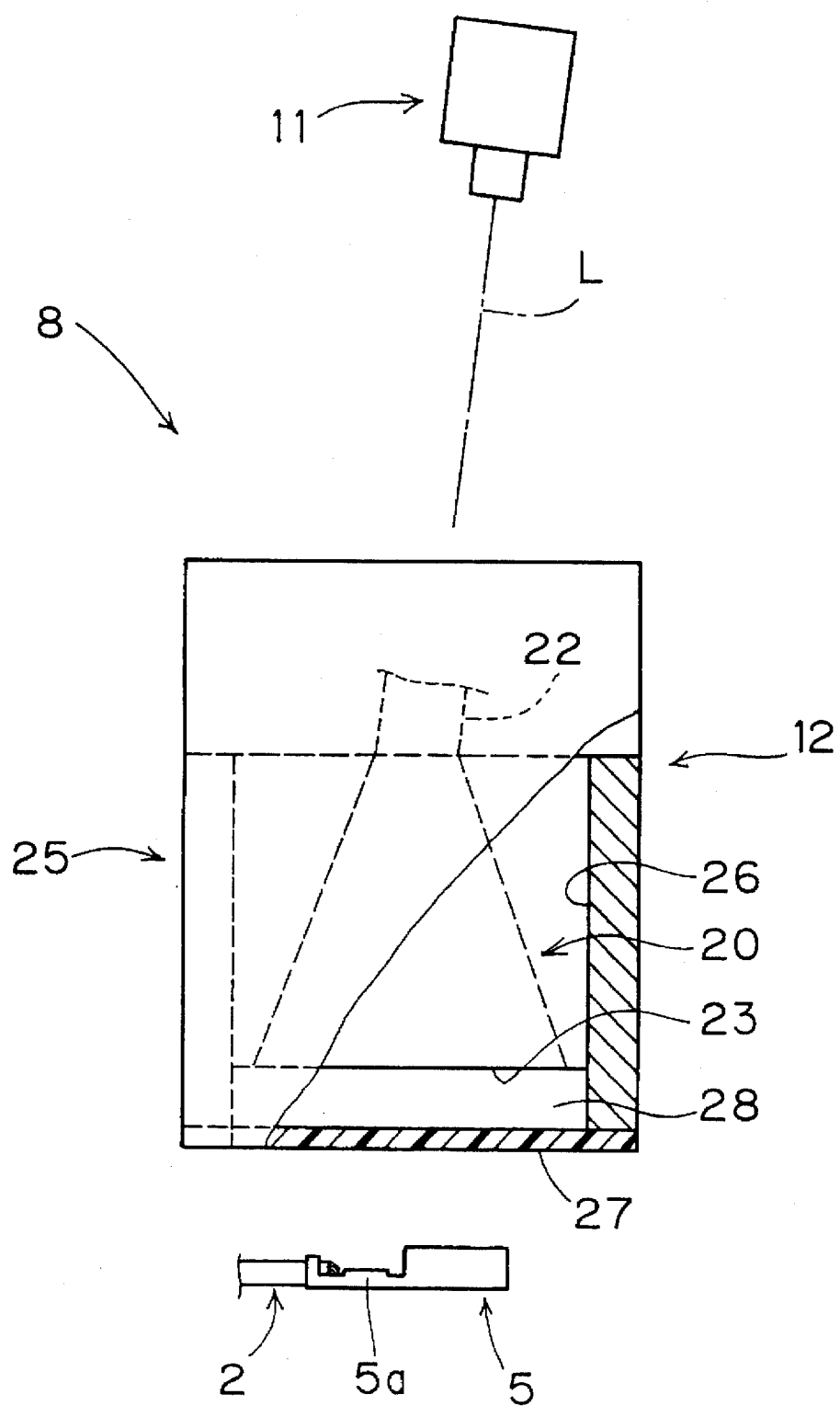
FIG. 5 is a right side view of FIG. 4.

As shown in FIGS. 4 and 5, the illuminating means 12 includes a pair of illuminating portions 20 located on opposite sides of a photographing path 19 of the image pickup camera 11 for directing illumination in substantially the same direction as the photographing direction of the image pickup camera 11 toward the end of the cable 2 passing therethrough along the bidirectional path P, a lamp housing 21 located in a separate position and includes a light source such as a halogen lamp, and optical fibers 22 made of quartz, plastic and the like for guiding the light emitted from light source to the pair of illuminating portions 20.

The distal end of each optical fibers 22 adjacent the illuminating portions 20 is of a flat and fan-shaped configuration flared gradually toward the end. Light projecting portions 23 at the distal ends are held by cuboid-shaped fiber array holders 24 so that they are elongated in substantially the same direction as the longitudinal direction of the cable 2 passing therethrough. The fiber array holders 24 are securely mounted in an illumination holder 25.

The photographing path 19 defined by a rectangular aperture along an optical axis L of the image pickup camera 11 is formed centrally of the illumination holder 25 which in turn includes similarly rectangular illuminating portion mounting apertures 26 on opposite sides of the photographing path 19. The fiber array holders 24 are respectively inserted from above into the illuminating portion mounting apertures 26 and securely mounted in the illumination holder 25 with screws and the like.

Transmitted light scattering plates 27 made of ground glass or acrylic board are securely mounted with screws and the like on the bottom of the illuminating portion mounting apertures 26 suitably spaced apart from the light projecting portions 23 of the optical fibers 22. Spacings surrounded by the light projecting portions 23 and transmitted light scattering plates 27 are defined as spacings 28 for diffusing the light guided by the optical fibers 22.

The illumination holder 25 is mounted in a predetermined attitude to a mounting bracket 29 on the base of the stripped terminal crimping machine 1.

The detecting means 13 includes a first sensor 31 for detecting the timing of photographing the end of the cable 2 transported in one direction (a first direction) along the bidirectional path P by the image pickup camera 11, and a second sensor 32 for detecting the timing of photographing the end of the cable 2 transported in the opposite direction (a second direction) along the bidirectional path P by the image pickup camera 11. The sensors 31, 32 are mounted to a sensor mounting bracket 33 in a position deviated from the optical axis L of the image pickup camera 11.

Figure 2:
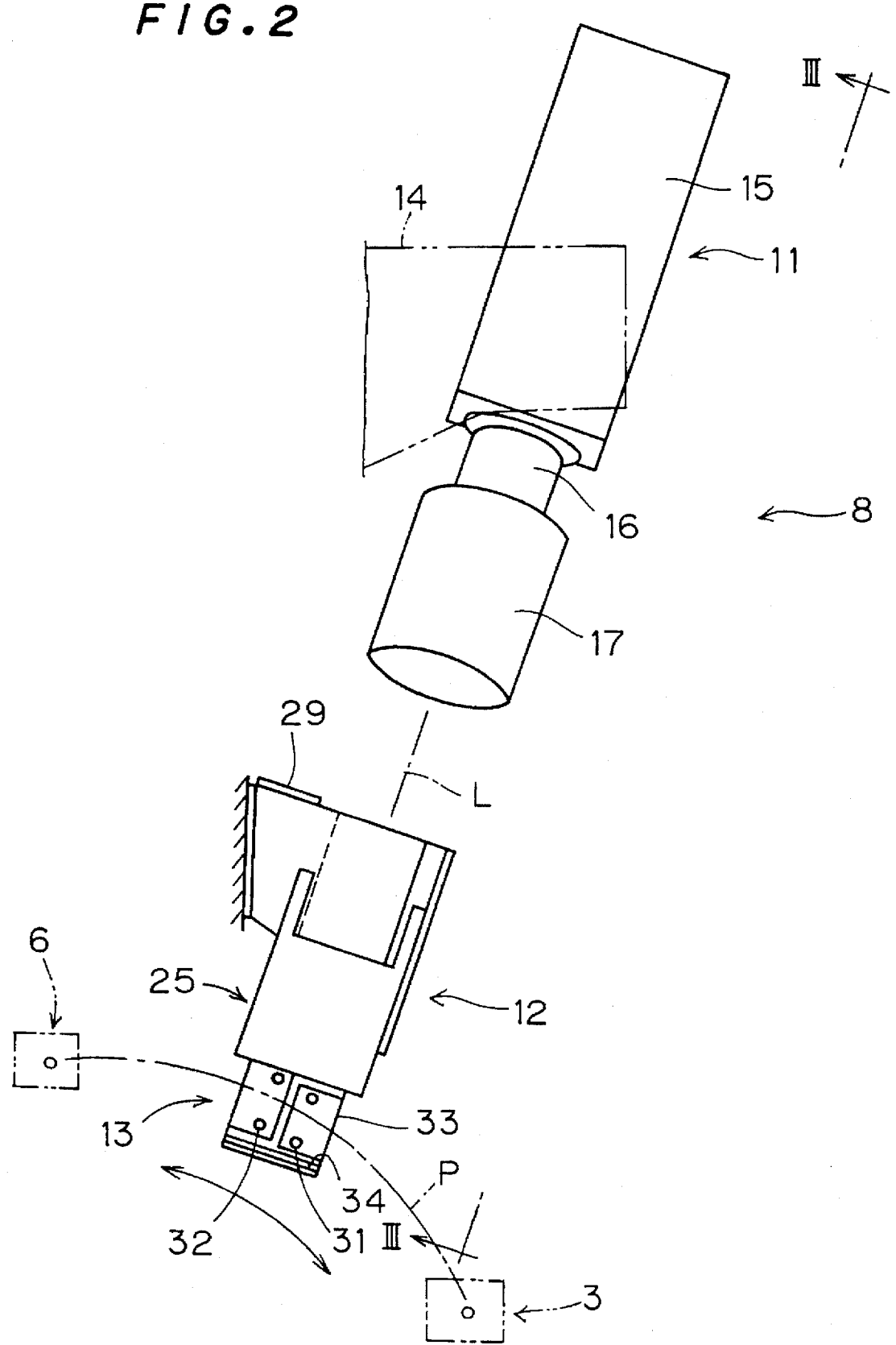
FIG. 2 schematically illustrates a terminated cable portion inspection device for the stripped terminal crimping machine according to the preferred embodiment of the present invention.
Figure 3:
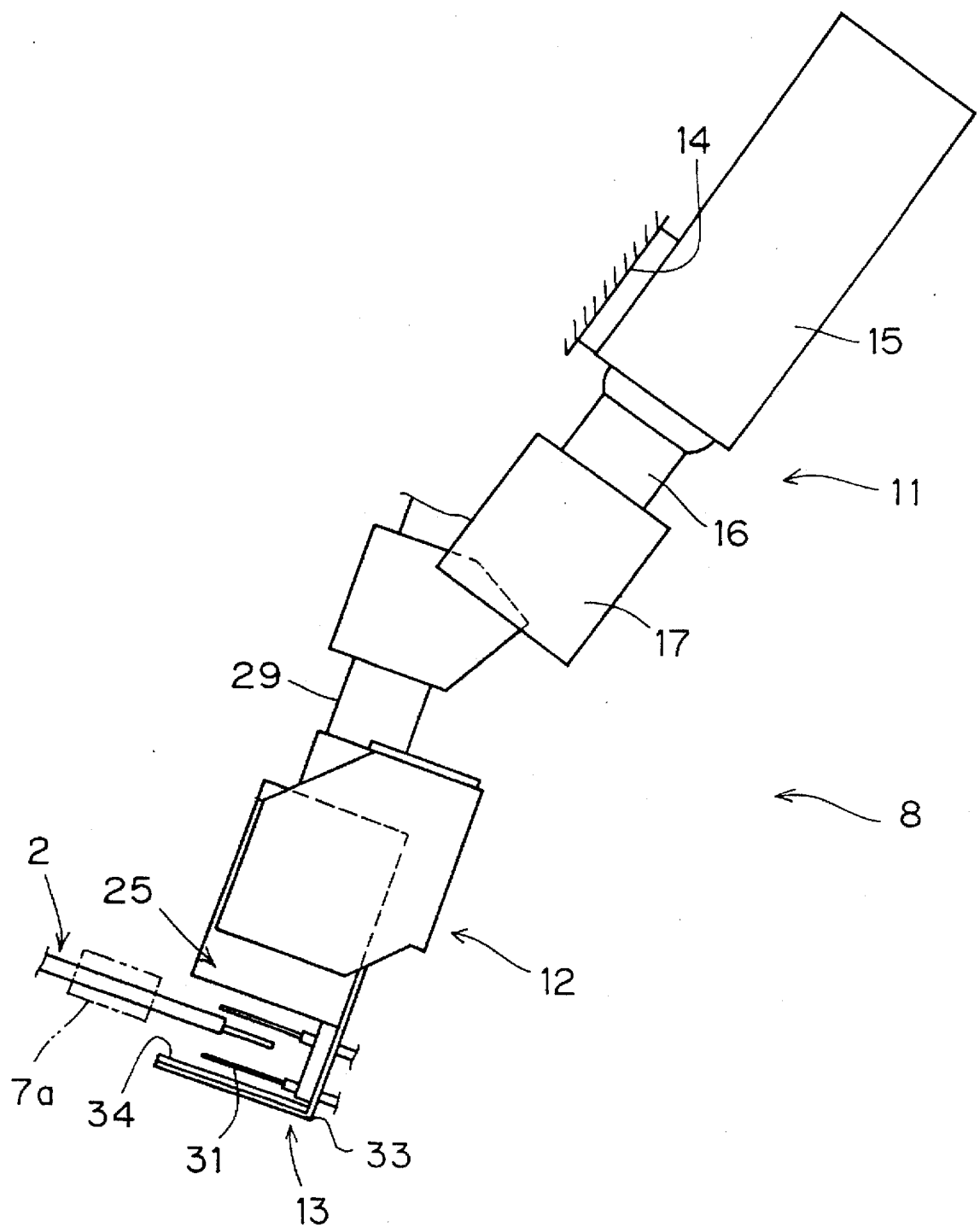
FIG. 3 is a view in the direction of the arrows III—III of FIG. 2.

Each of the sensors 31, 32 includes a light projector and a light receiver which are spaced apart in the direction of the optical axis L on opposite sides of the bidirectional path P as shown in FIGS. 2 to 4.

Figure 6:
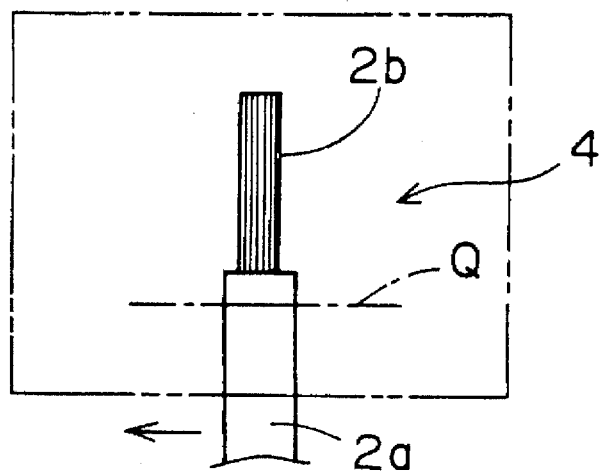
FIG. 6 illustrates a photographed image of a cable end transported in a first direction.
Figure 7:
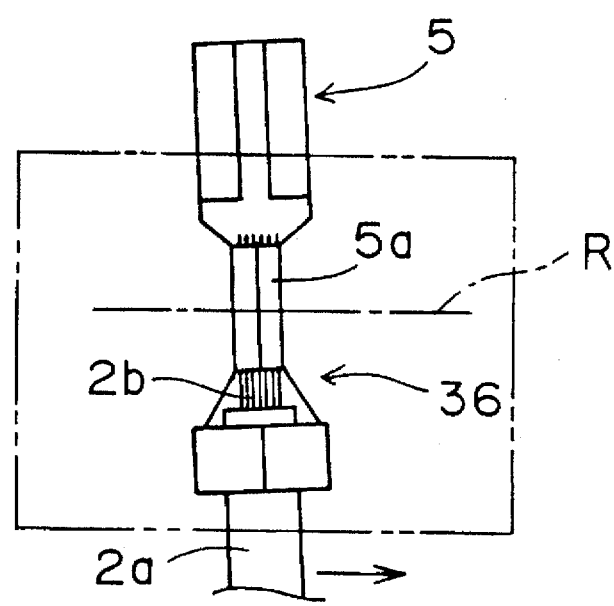
FIG. 7 illustrates a photographed image of the cable end transported in a second direction.

A detecting position C of the first sensor 31 is located in corresponding relation to the passing position of the end of the coating 2a of the stripped cable 2 as shown in FIG. 6, and a detecting position R of the second sensor 32 is located in corresponding relation to the passing position of an intermediate portion of a core barrel portion 5a serving as a core crimping portion for crimping the crimp terminal 5 to a core portion 2b as shown in FIG. 7. The photographing range of the image pickup camera 11 is shown in phantom in FIGS. 6 and 7.

An irregular reflector plate 34 serving as a sub-illuminating means is mounted over the bottom surface of the sensor mounting bracket 33 opposed to the illuminating portions 20 to direct illumination in the direction opposite from the illuminating portions 20 toward the end of the cable 2 passing therethrough along the bidirectional path P. The optical axis L of the image pickup camera 11 is slightly inclined toward the end surface at the end of the cable 2 from the direction orthogonal to the longitudinal direction of the cable 2 passing through the photographing position for ease of recognition as shown in FIG. 5.

In the preferred embodiment of the present invention as above constructed, the end of the cable 2 fed from a cable feeding portion not shown to the cable clamp portion 7a of the transport arm 7 is held by the cable clamp portion 7a and subjected to the stripping of the coating 2a in the stripping portion 3.

Upon completion of the stripping, the transport arm 7 is pivoted on the support shaft 9 to transport the stripped portion 4 at the end of the cable 2 in the first direction from an initial position of the bidirectional path P. In the course of the transport, the first sensor 31 detects the end of the cable 2 to actuate a timer, and the image pickup camera 11 is controlled so that the shutter fires when the stripped portion 4 passes through the position of the optical axis L.

As the end of the cable 2 reaches the terminal crimping portion 6, the crimp terminal 5 is crimped to the stripped portion 4. Upon completion of the crimping, the transport arm 7 is pivoted on the support shaft 9 to transport a terminal crimped portion 36 at the end of the cable 2 in the second direction along the bidirectional path P from the terminal crimping portion 6. In the course of the transport, the second sensor 32 detects the end of the cable 2 to actuate the timer, and the image pickup camera 11 is controlled so that the shutter fires when the terminal crimped portion 36 passes through the position of the optical axis L.

On arrival at the initial position in the stripping portion 3, the cable 2 is transported by a predetermined length in a predetermined direction and cut in position. The stripping and terminal crimping are repeatedly performed on successive cables 2 in sequential order in the same fashion, and the stripped portion 4 and terminal crimped portion 36 of the successive cables 2 are photographed during the transport of the end thereof and subjected to the conventional image processing and judgement whether the stripping and crimping conditions are defective or not.

According to the preferred embodiment, as above stated, a sufficient brightness is ensured by the illuminating portions 20 on opposite sides of the photographing path 19 of the image pickup camera 11 for directing the illumination in substantially the same direction as the photographing direction of the image pickup camera 11 toward the end of the cable 2 passing therethrough along the bidirectional path P and each elongated in substantially the same direction as the longitudinal direction of the transported cable 2. This allows the high-shutter-speed image pickup camera 11 to satisfactorily capture the reflected image of the end of the cable 2 moving at high speeds, thereby providing a great amount of image information and achieving inspection using more correct image information and improvement in inspection reliability.

Further, the light emitted from the light source in the lamp housing 21 located in a vacant spacing in the separate position is designed to be guided to the light projecting portions 23 of the illuminating portions 20 by the optical fibers 22, permitting the illuminating portions 20 which are compact in size to be readily incorporated in a small spacing in the stripped terminal crimping machine 1 in closer proximity to the bidirectional path P of the end of the cable 2. This also insures the sufficient brightness and the size reduction of the terminated cable portion inspection device 8 itself incorporated in the stripped terminal crimping machine 1.

Since the detecting position Q of the first sensor 31 is located in corresponding relation to the passing position of the end of the coating 2a at the stripped end of the cable 2, the passage of the end of the cable 2 which might suffer a failure such as disconnection of the core portion 2b is satisfactorily detected. Since the detecting position R of the second sensor 32 is located in corresponding relation to the passing position of the intermediate portion of the core barrel portion 5a of the crimped crimp terminal 5, the detecting position R is a generally intermediate position of the photographing range as shown in FIG. 7, which can effectively solve the yawing problem of the crimp terminal 5. This provides good photographing timing by the image pickup camera 11, whether the cable 2 be transported in the first or second direction along the bidirectional path P, and stabilized image capturing.

The end of the cable 2 held in cantilevered fashion by the cable clamp portion 7a during the high-speed transport causes the distal end of the stripped portion 4 to deflect slightly rearwardly in the transport direction when transported in the first direction along the bidirectional path P. The end of the cable 2 weighted by the crimp terminal 5 crimped thereto when transported in the second direction along the bidirectional path P causes the distal end of the terminal crimped portion 36 to deflect by a greater amount rearwardly in the opposite transport direction. However, the provision of the respective purpose-built first and second sensors 31 and 32 can provide good photographing timing by the image pickup camera 11 and stabilized image capturing.

The light diffusing spacings 28 between the light projecting portions 23 and the transmitted light scattering plates 27 can produce uniformly scattered light for the end of the cable 2 passing along the bidirectional path P to provide illumination of high brightness. Such a structure that the diffusing spacings 28 are merely provided may reduce the costs.

Figure 8:
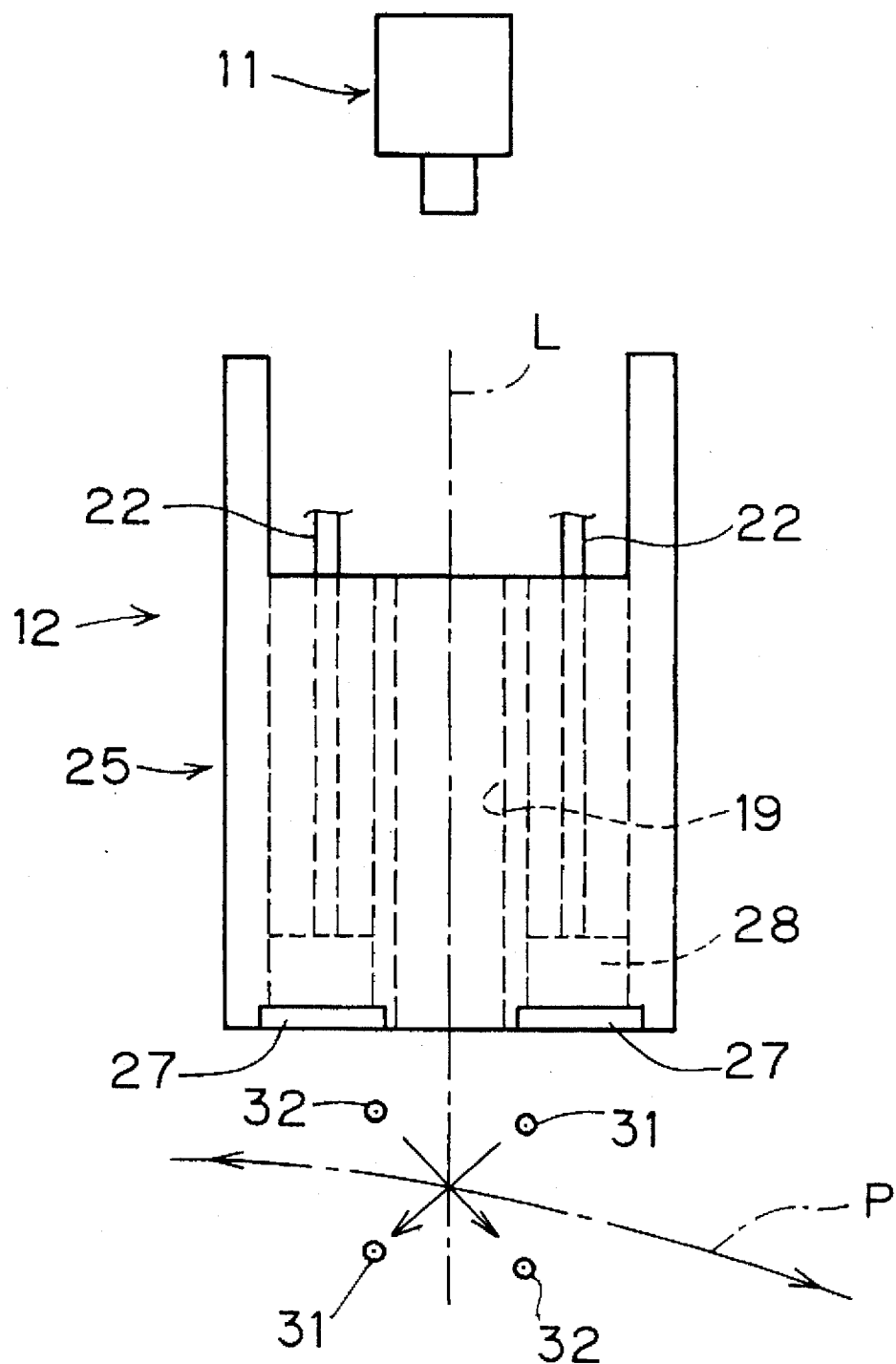
FIG. 8 illustrates another preferred embodiment according to the present invention.

FIG. 8 illustrates another preferred embodiment according to the present invention wherein the light projectors and light receivers of the first and second sensors 31 and 32 are opposed to cross the intersection of the bidirectional path P and optical axis L. In this case, the above described timer control is not required, and the shutter of the image pickup camera 11 fires simultaneously with the detection of the end of the cable 2 by the first and second sensors 31, 32.

Figure 9:
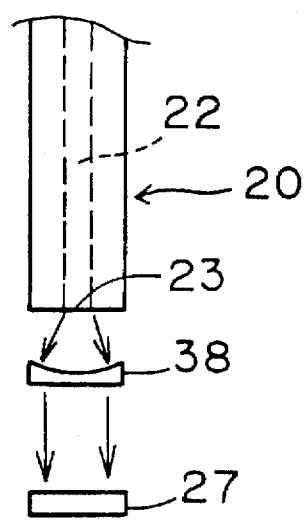
FIG. 9 illustrates another preferred embodiment according to the present invention.
Figure 10:
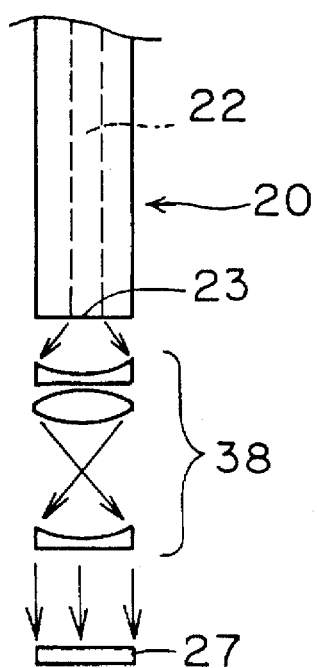
FIG. 10 illustrates another preferred embodiment according to the present invention.

Referring to FIGS. 9 and 10, one or more condenser lenses 38 may be suitably provided between the light projecting portion 23 and transmitted light scattering plate 27 to guide the light from the light projecting portion 23 in a direction at right angles to the transmitted light scattering plate 27. This provides illumination of higher brightness by more uniformly scattered light.

In the first and second preferred embodiments, the illuminating portions are mounted in the illuminating portion mounting apertures 26 of the illumination holder 25. However, the illuminating portions 20 may be separately independently mounted to the base of the stripped terminal crimping machine 1.

The processing of the photographed reflected image is discussed below using the image of the terminal crimped portion 36 transported in the second direction along the bidirectional path P.

Figure 11:
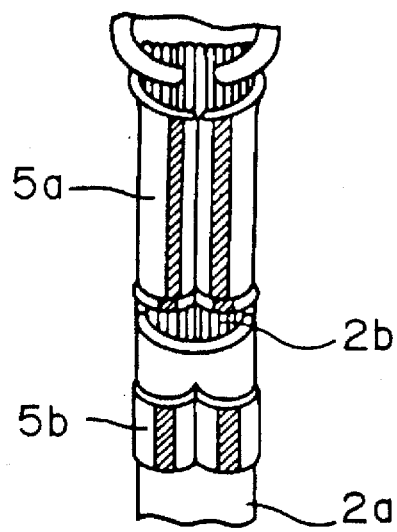
FIG. 11 illustrates an image of the cable end transported in the second direction of the first preferred embodiment.
Figure 12:
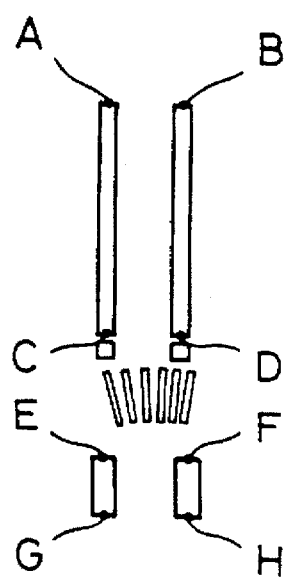
FIGS. 12–16, 17A–17C, 18A and 18B illustrate image processing of the first preferred embodiment.

An example of the image of the terminal crimped portion 36 transported in the second direction is shown in FIG. 11. The shaded portions of FIG. 11 are specular reflection portions. Specular reflection is also provided in the core portion 2b between a resin barrel portion 5b and the core barrel portion 5a. The specular reflection portions are extracted as shown in FIG. 12.

In general, bellmouths are formed on opposite ends of the core barrel portion 5a to release the stresses during the crimping of the crimp terminal 5. The bellmouths sharpen the boundary between the end of the specular reflection portions in the core barrel portion 5 and the core portion 2b.

Reference points for the image processing are derived by the image processing means by means of the run-length encoding technique which is based on the derivation of the configuration and the like of the crimp terminal 5 to be processed from the changes in white and black information along one scanning line.

Figure 13:
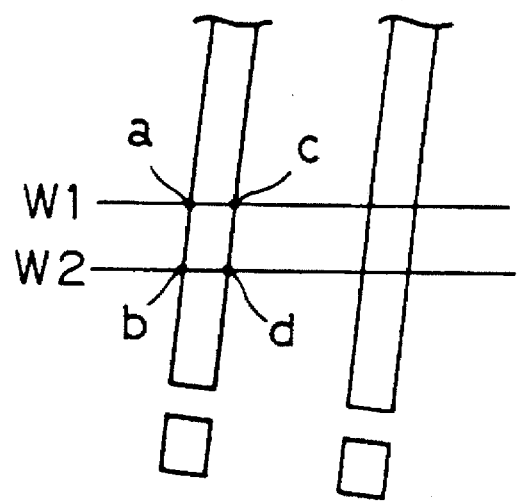
Figure 14:
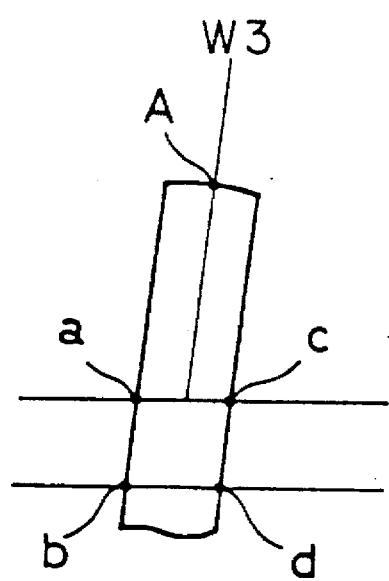

Specifically, to detect the reference points required for the image processing, two linear windows W1, W2 are established in the middle of the image of the specular reflection portions in the core barrel portion 5a as shown in FIG. 13. The points a, b, c, d of intersection of the windows W1, W2 and the borders of the specular reflection portions are derived. The gradient of the specular reflection portions is determined from the gradient of the line segment ab connecting the points a and b. Then, as shown in FIG. 14, a window W3 is established which extends from the mid-point of the line segment ac or any intermediate point on the line segment ac with a gradient of the line segment ab. A point A of change in brightness is derived on the window W3 and serves as one of the reference points required for the image processing. Likewise, other reference points B, C, D, E, F, G, H shown in FIG. 12 are derived.

In practice, the barrel portions 5a and 5b are not completely formed in a cylindrical shape and provide incomplete specular surfaces to cause a geometrically unstable shape of the specular reflection portions. It is hence impracticable to determine the reference points during one process shown in FIGS. 13 and 14, and the reference points are in practice determined by repeating the process twice or three times.

Figure 15:
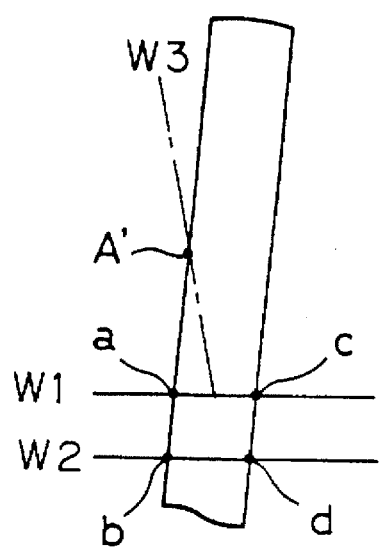
Figure 16:
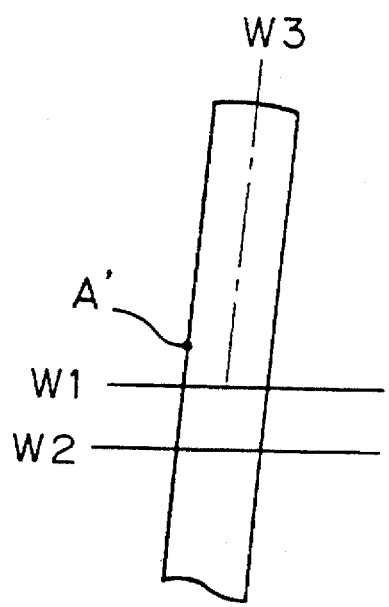

More specifically, if the window W3 is established as shown in FIG. 15 due to a gradient error based on the line segment ab of FIG. 14, a reference point A' is not located at the end of the specular reflection portion. In this case, the windows W1, W2 are re-established at the positions shifted by several pixels from the derived reference point A' and the similar operation is repeated to derive the point of change in brightness on the window W3.

In this manner, the repetition of the establishment of the window W3 and derivation of the brightness change point twice or three times can accurately derive the reference point A (FIG. 14).

After the reference points A to H required for the image processing are derived by the above noted procedure, the configuration, size and gradient of the crimp terminal 5 are determined on the basis of the reference points A to H, and a judgement is made whether or not the crimping conditions of the crimp terminal 5 are defective on the basis of the position of the end of the coating 2a between the resin barrel portion 5b and core barrel portion 5a and the length of projecting core portion 2b between the core barrel portion 5a and a front end connecting portion.

The attitude of the crimp terminal 5 need not be completely the same because of the correct derivation of the reference points A to H. This allows an acceptable level of rough arrangement of the crimp terminal 5 to be inspected. A stable image is obtained if the crimp terminal 5 falls within the photographing range of the image pickup camera 11.

Figure 17A:
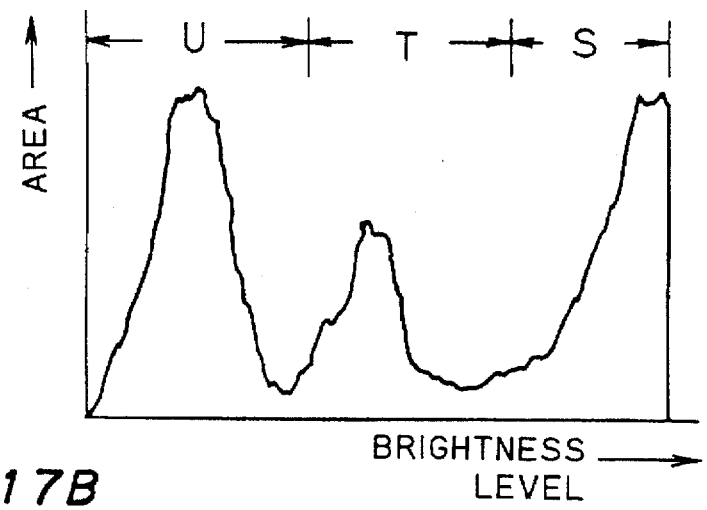

A distribution curve based on an area versus received light intensity histogram for an image of the crimp terminal 5 crimped to a blue cable 2 illuminated by the illuminating means 12 is shown, for example, in FIG. 17A wherein the abscissa is a brightness level indicated by 256 gradations and the ordinate is the area (the number of pixels). In FIG. 17A, the region of high brightness level corresponds to a specular reflection region S in the barrel portions 5a, 5b of the crimp terminal 5, the region of intermediate brightness level corresponds to a resin region T of the coating 2a of the cable 2, and the region of low brightness level corresponds to a non-specular reflection region U of the crimp terminal 5. In the distribution curve of FIG. 17A based on the area versus received light intensity histogram, there are valleys between the specular reflection region S and resin region T and between the resin region T and non-specular reflection region U.

Figure 17B:
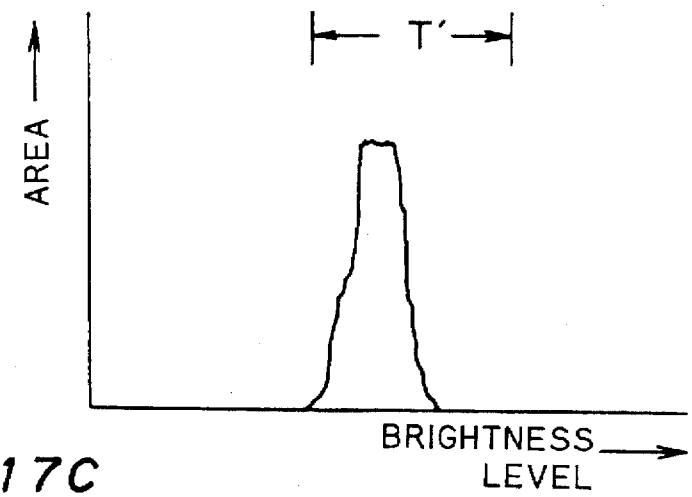

A distribution curve based on an area versus received light intensity histogram for a background image including no crimp terminal 5 is shown in FIG. 17B. There is a peak in a background region T' corresponding to the resin region T. The irregular reflector plate 34 is selected so that the background region T' is positioned intermediate the specular reflection region S and non-specular reflection region U of FIG. 17A.

Figure 17C:
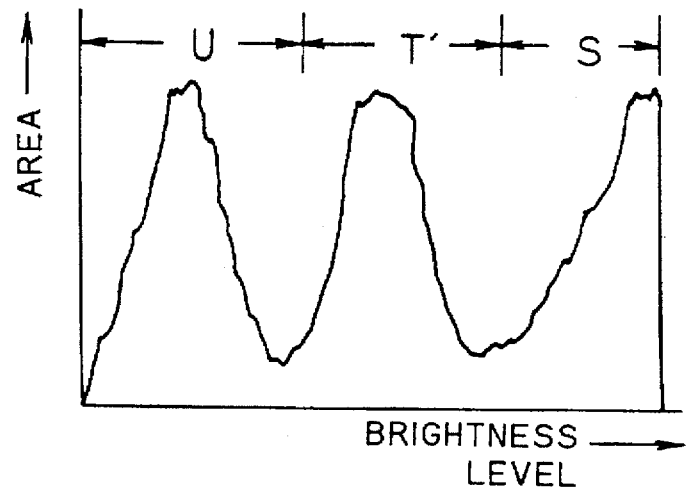

The synthesis of the distribution curves of FIGS. 17A and 17B based on the area versus received light intensity histograms is shown in FIG. 17C. In FIG. 17C, there are peaks in the specular reflection region S, background region T', and non-specular reflection region U, and there are valleys between the regions S and T' and between the regions T' and U, similarly to FIG. 17A.

For the blue cable 2, a typical distribution curve based on the area versus received light intensity histogram for the crimp terminal 5 is previously determined, and binary levels may be set between the specular reflection region S and background region T' and between the background region T' and non-specular reflection region U, that is, in the valleys of the distribution curve.

Figure 18A:
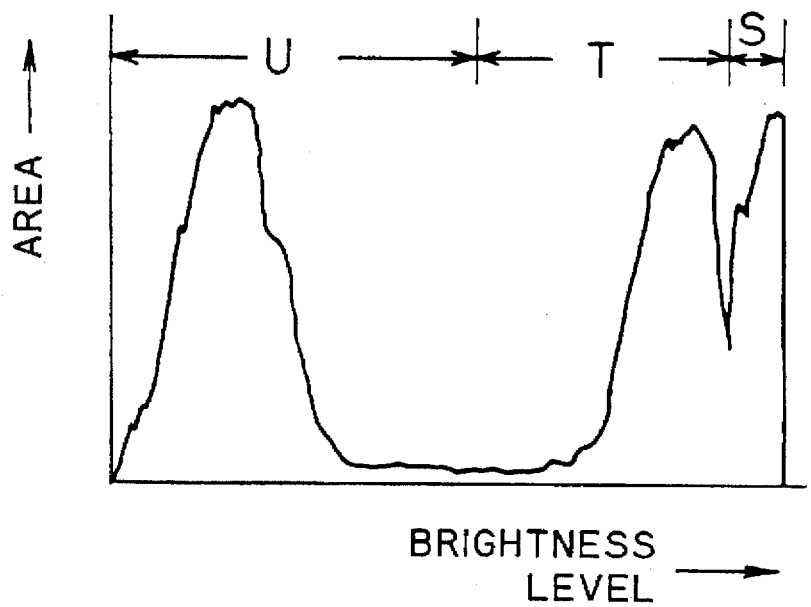
Figure 18B:
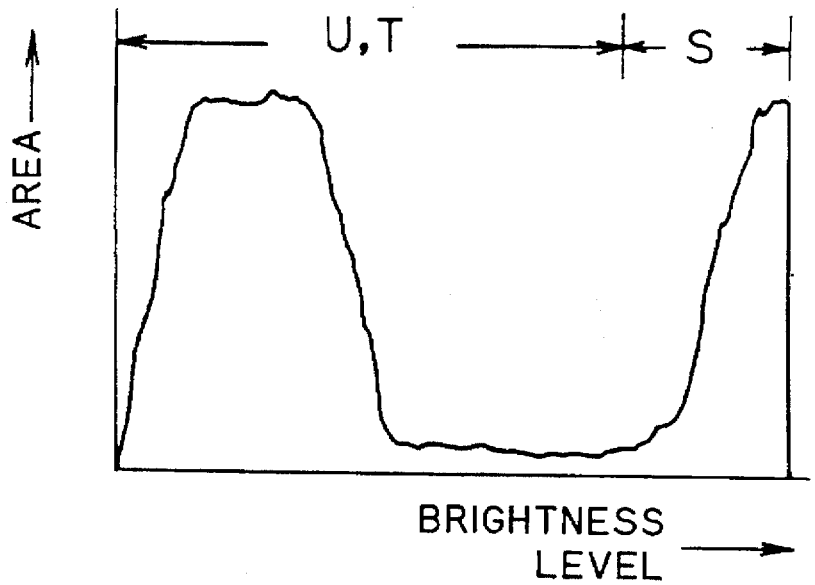

Distribution curves based on area versus received light intensity histograms when the cable 2 is white and black are shown in FIGS. 18A and 18B, respectively. With the while cable, the peak in the resin region T is shifted toward the specular reflection region S as compared with the blue cable (FIG. 17A) and there is a small valley between the regions S and T. With the black cable, the peak in the resin region T is shifted toward the non-specular reflection region U as compared with the blue cable, and the resin region T and non-specular reflection region U overlap so that the distinction therebetween is blurry. However, in the case of the white cable, the binary level may be set between the specular reflection region S and resin region T by regulating the illumination intensity using the diaphragm of the lens of the image pickup camera 11. This allows the setting of two different binary levels, that is, the above stated binary level between the specular reflection region S and resin region T and the binary level between the resin region T and non-specular reflection region U. In the case of the black cable, one binary level is reliably set in a wide, distinct valley between the resin and non-specular reflection regions T, U and the specular reflection region S.

Thus two binary levels may be set for the while cable 2, similar to the blue cable, by previously determining the typical distribution curve based on the area versus received light intensity histogram for the crimp terminal 5. For the black cable, although one binary level may be definitely set on the basis of the distribution curve, another binary level may be readily set in a low brightness level region, if required, on the basis of various distribution curves based on area versus received light intensity histograms.

The setting of two different binary levels on the basis of the distribution curve based on the area versus received light intensity histogram for the image of the crimp terminal 5 toward which illumination is directed by the illuminating portions 20 and irregular reflector plate 34 in opposite directions insures the detection of the core portion 2b extending off, particularly the core portion 2b extending off sidewise.

For example, when the crimp terminal 5 is crimped to the cable, with one core M extending off over the core barrel portion 5a as shown in FIGS. 19A and 19B, then the extending-off core M reflects light from the illuminating portions 20 as shown by the arrows of FIG. 20 which is an enlarged sectional view taken along the line X–X' of FIG. 19A. Since this reflection causes partially irregular reflection in the specular reflection portions in the core barrel portion 5a, the core M extending off over the core barrel portion 5a is definitely detected by the binary processing using one binary level. Therefore, the core M extending off over the core barrel portion 5a is detected by the presence of partially irregular reflection in the specular reflection portions in the core barrel portion 5a. FIG. 19B is a front view of FIG. 19A which is a plan view.

Figure 21:
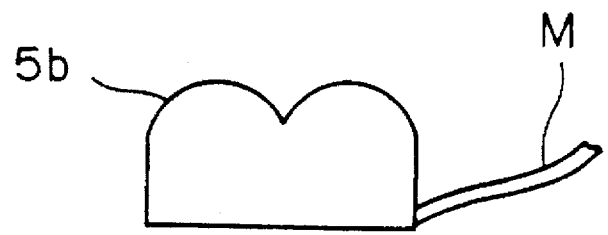
Figure 22:
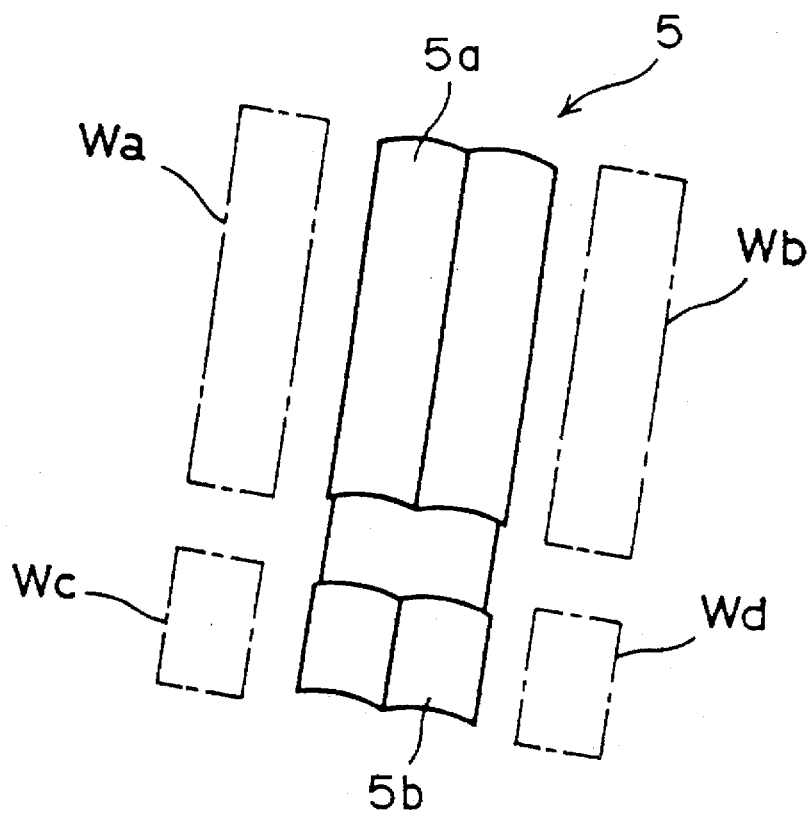
FIGS. 22 and 23 illustrate image processing of the first preferred embodiment.
Figure 23:
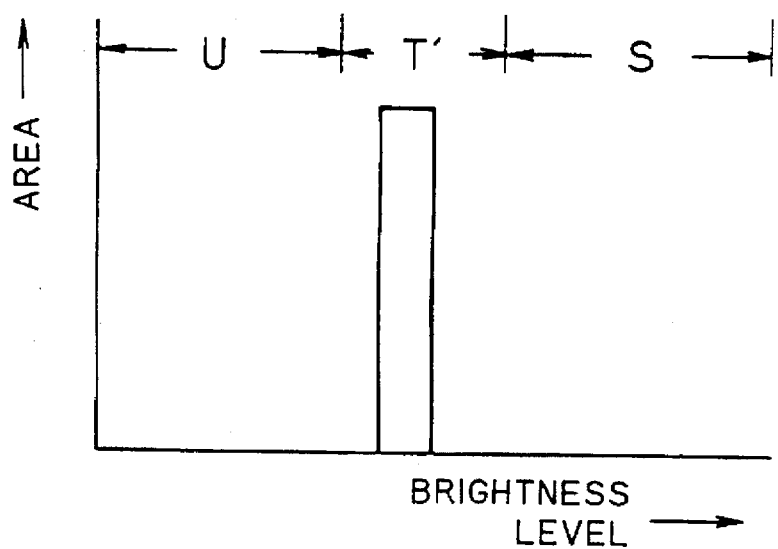

When the core M is extending off sidewise from the crimp terminal 5 as shown in FIG. 21, the illuminating portions 20 and irregular reflector plate 34 direct illumination in the opposite directions toward the crimp terminal 5 to obtain an image of the crimp terminal 5. On the image of the crimp terminal 5 as shown in FIG. 22, rectangular windows Wa, Wb are established on opposite sides of the core barrel portion 5a and rectangular windows Wc, Wd are similarly established on opposite sides of the resin barrel portion 5b. The distribution curve based on the area versus received light intensity histogram for the windows Wa to Wd is shown in FIG. 23 if the core M does not extend off. In the distribution curve of FIG. 23, there is a peak only in the background region T', and no peaks appear in the regions S and U.

The core M extending off sidewise from the crimp terminal 5 generates a peak in the region S or U in addition to the peak in the background region T' in the distribution curve for any of the windows Wa to Wd. Thus the binary processing is performed on the brightness of each pixel in each of the windows Wa to Wd on the basis of the binary levels set between the regions S an T' and between regions T' and U, and the presence of a pixel having a brightness higher than the higher binary level between the regions S and T' and a pixel having a brightness lower than the lower binary level between the regions T' and U is detected, thereby detecting the core M extending off sidewise from the crimp terminal 5 in any direction.

Figures 24A, 24B:
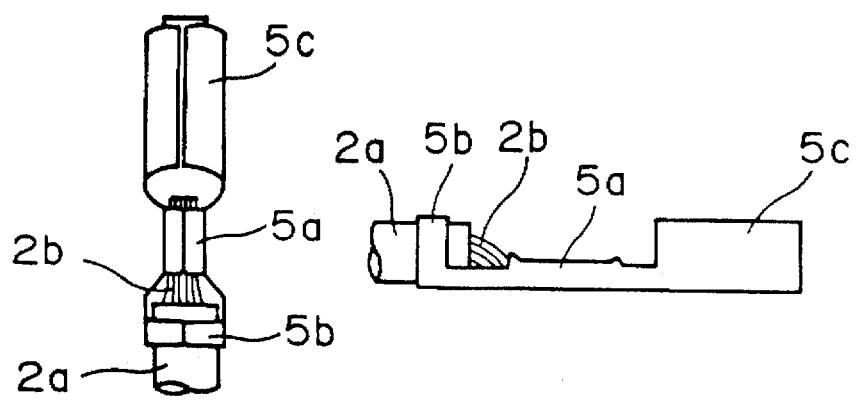
FIGS. 24A, 24B, 25A, 25B, 26A and 26B illustrate operation of the first preferred embodiment.

As a result of the image processing, it is judged that the crimping conditions of the crimp terminal 5 are good, when the resin barrel portion 5b grasps the coating 2a, with the coating 2a of the cable 2 extending by a suitable length between the resin barrel portion 5b and core barrel portion 5a of the crimp terminal 5, and the core barrel portion 5a grasps the core portion 2b, with the core portion 2b slightly exposed between the core barrel portion 5a and a front end connecting portion 5c, as shown in FIGS. 24A and 24B.

Figures 25A, 25B:
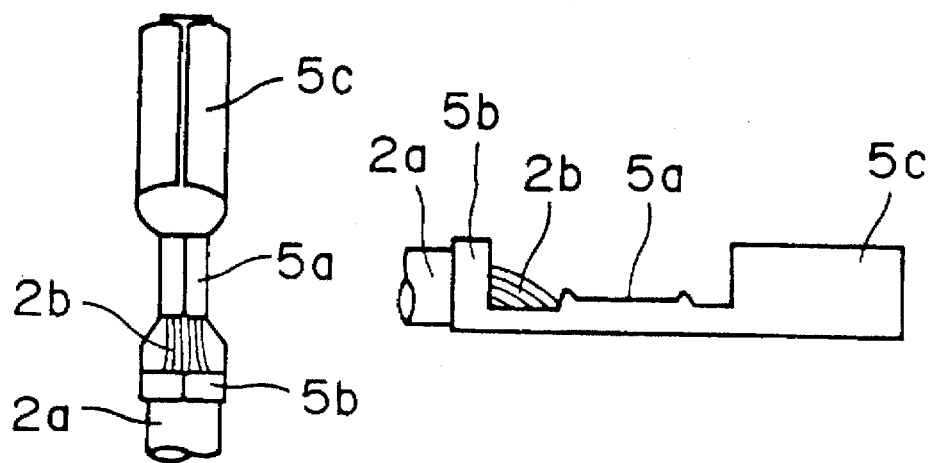

As a result of the image processing, a so-called resin portion crimping failure is judged, when the coating 2a of the cable 2 does not appear between the resin barrel portion 5b and core barrel portion 5a of the crimp terminal 5 and the resin barrel portion 5b grasps the end of the coating 2a as shown in FIGS. 25A and 25B.

Figures 26A, 26B:
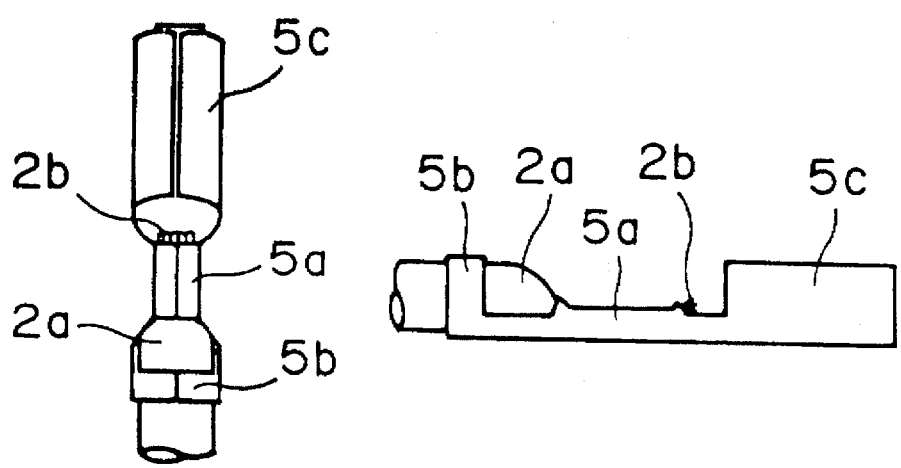

As a result of the image processing, a so-called resin engagement failure is judged, when the core barrel portion 5a of the crimp terminal 5 grasps the end of the coating 2a and the core portion 2b does not appear between the resin barrel portion 5b and core barrel portion 5a as shown in FIGS. 26A and 26B.

Other failures may be detected as a result of the image processing, for example, the above stated core extending-off failure, a so-called pressing failure in which the resin barrel portion 5b is open, and a short core failure in which no end of the core portion 2b extends from the core barrel portion 5a. These failures detected are subjected to suitable corrective actions.

Although the image processing of the terminal crimped portion 36 fed in the second direction along the bidirectional path P has been described above, the image processing of the stripped portion 4 fed in the first direction therealong may be similarly performed.

In the processing using the photographed reflected image, other image processing methods may be used for quality judgement.

While the invention has been shown and described in detail, the foregoing description is in all aspects illustrative and not restrictive. It is therefore understood that numerous modifications and variations can be devised without departing from the scope of the invention.

What is claimed is:

1. In a stripped terminal crimping machine including a stripping portion for stripping a coating at an end of a cable, a terminal crimping portion for crimping a crimp terminal to the stripped end of the cable, a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, and a terminated cable portion inspection device for photographing the cable end transported along the bidirectional path to inspect a stripped portion and a terminal crimped portion of the cable by image processing;

said terminated cable portion inspection device comprising:

an image pickup camera having a high shutter speed;

a pair of illuminating portions on opposite sides of a photographing path of said image pickup camera for directing illumination in substantially the same direction as a photographing direction of said image pickup camera toward the cable end passing therethrough along the bidirectional path, said pair of illuminating portions being elongated in substantially the same direction as a longitudinal direction of the cable;

an optical fiber for guiding light emitted from a light source to light projecting portions of said illuminating portions;

a first sensor for detecting a timing of photographing the cable end transported in the first direction along the bidirectional path by said image pickup camera; and a second sensor for detecting a timing of photographing the cable end transported in the second direction along the bidirectional path by said image pickup camera, said first sensor and said second sensor being located in positions deviated from an optical axis of said image pickup camera.

2. In a stripped terminal crimping machine including a stripping portion for stripping a coating at an end of a cable, a terminal crimping portion for crimping a crimp terminal to the stripped end of the cable, a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, and a terminated cable portion inspection device for photographing the cable end transported along the bidirectional path to inspect a stripped portion and a terminal crimped portion of the cable by image processing;

said terminated cable portion inspection device comprising:

an image pickup camera having a high shutter speed;

a pair of illuminating portions on opposite sides of a photographing path of said image pickup camera for directing illumination in substantially the same direction as a photographing direction of said image pickup camera toward the cable end passing therethrough along the bidirectional path, said pair of illuminating portions being elongated in substantially the same direction as a longitudinal direction of the cable;

a first sensor for detecting a timing of photographing the cable end transported in the first direction along the bidirectional path by said image pickup camera; and a second sensor for detecting a timing of photographing the cable end transported in the second direction along the bidirectional path by said image pickup camera, said first sensor and said second sensor being located in positions deviated from an optical axis of said image pickup camera, wherein the detection position of said first sensor is positioned in corresponding relation to a passing position of an end of the coating at the stripped cable end, and the detection position of said second sensor is positioned in corresponding relation to a passing position of an intermediate portion of a core crimping portion of the crimped crimp terminal.

3. The terminated cable portion inspection device of claim 1, wherein the detection position of said first sensor is positioned in corresponding relation to a passing position of an end of the coating at the stripped cable end, and the detection position of said second sensor is positioned in corresponding relation to a passing position of an intermediate portion of a core crimping portion of the crimped crimp terminal.

4. The terminated cable portion inspection device of claim 1, wherein each of said pair of illuminating portions includes:

a transmitted light scattering plate between said bidirectional path and each of said light projecting portions projecting the light guided by said optical fiber; and a spacing between each of said light projecting portions and said transmitted light scattering plate for diffusing light.

5. The terminated cable portion inspection device of claim 1, wherein each of said pair of illuminating portions includes:

a transmitted light scattering plate between said bidirectional path and each of said light projecting portions projecting the light guided by said optical fiber; and a condenser lens between each of said light projecting portions and said transmitted light scattering plate for guiding the light projected from each of said light projecting portions in a direction at right angles to said transmitted light scattering plate.

6. The terminated cable portion inspection device of claim 1, wherein said first sensor and said second sensor are positioned so that the cable end is detected by said first sensor and said second sensor when the cable end passes across the optical axis of said image pickup camera.

7. The terminated cable portion inspection device of claim 2, wherein said first sensor and said second sensor are positioned so that the cable end is detected by said first sensor and said second sensor when the cable end passes across the optical axis of said image pickup camera.

8. The terminated cable portion inspection device of claim 1, further comprising:

an irregular reflector plate opposed to said illuminating portions, with the bidirectional path therebetween.

* * * * *